United States Patent
Knifton et al.

(10) Patent No.: US 6,706,656 B2
(45) Date of Patent: Mar. 16, 2004

(54) ONE STEP PROCESS FOR PREPARING A 1,3-DIOL

(75) Inventors: John Frederick Knifton, Houston, TX (US); Lynn Henry Slaugh, Houston, TX (US); Paul Richard Weider, Houston, TX (US); Talmadge Gail James, Houston, TX (US); Joseph Broun Powell, Houston, TX (US); Kevin Dale Allen, Katy, TX (US); Timothy Scott Williams, Houston, TX (US)

(73) Assignee: Shell Oil Company, Houston, TX (US)

( * ) Notice: Subject to any disclaimer, the term of this patent is extended or adjusted under 35 U.S.C. 154(b) by 192 days.

(21) Appl. No.: 10/127,957

(22) Filed: Apr. 23, 2002

(65) Prior Publication Data

US 2002/0161251 A1 Oct. 31, 2002

Related U.S. Application Data

(62) Division of application No. 09/808,974, filed on Mar. 15, 2001, now Pat. No. 6,469,222.
(60) Provisional application No. 60/192,191, filed on Mar. 27, 2000.

(51) Int. Cl.$^7$ .......................... B01J 31/00; B01J 27/185
(52) U.S. Cl. ........................ 502/154; 502/161; 502/162; 502/150; 502/152; 502/171; 502/208; 502/213
(58) Field of Search ................................. 502/150, 152, 502/154, 161, 162, 171, 208, 213

(56) References Cited

U.S. PATENT DOCUMENTS

| | | | |
|---|---|---|---|
| 4,253,987 A | 3/1981 | Fiato | 252/429 R |
| 4,451,680 A | 5/1984 | Knifton | 568/909 |
| 4,873,378 A | 10/1989 | Murphy et al. | 568/867 |
| 4,895,818 A | 1/1990 | Duggan et al. | 502/161 |
| 5,053,562 A | 10/1991 | Tau | 568/867 |
| 5,304,691 A | 4/1994 | Arhancet et al. | 568/867 |
| 5,360,939 A | 11/1994 | Stanley et al. | 568/454 |

OTHER PUBLICATIONS

U.S. patent application Ser. No. 09/957,561, Knifton et al., filed Sep. 20, 2001.
U.S. patent application Ser. No. 09/963,068, Allen et al., filed Sep. 25, 2001.

*Primary Examiner*—Johann R. Richter
*Assistant Examiner*—Elvis O. Price

(57) ABSTRACT

The invention provides a process for an improved oxirane hydroformylation catalyst, the improved oxirane hydroformylation catalyst, and a one step process for preparing a 1,3-diol in the presence of such a catalyst. One process for preparing the hydroformylation catalyst involves:

a) forming a complex (A) by contacting a ruthenium(0) compound with a ditertiary phosphine ligand; and
b) forming a complex (B) by subjecting complex (A) to a redox reaction with a cobalt(0) carbonyl compound. This catalyst is used in a one step hydroformylation process for preparing a 1,3-diol, comprising the reaction of an oxirane with syngas at hydroformylation conditions in an inert solvent in the presence of the above hydroformylation catalyst where recovery of product is preferably accomplished via phase separation of a diol rich phase from the bulk reaction liquor.

23 Claims, 3 Drawing Sheets

Figure 3
IR Spectra of Catalyst Regions

ONE STEP PROCESS FOR PREPARING A 1,3-DIOL

This is a division of Ser. No. 09/808,974 filed Mar. 15, 2001 now U.S. Pat. No. 6,469,222, which claims benefit of provisional application 60/192,191 filed Mar. 27, 2000.

FIELD OF THE INVENTION

The present invention relates to a one step process for preparing a 1,3-diol, and 1,3-propanediol in particular.

BACKGROUND OF THE INVENTION 1,3-Diols have plenty of uses, particularly in the synthesis of polymers. For instance, "CORTERRA" (trademark) is a polyester made of 1,3-propanediol (hereinafter 'PDO') and terephthalic acid, which polymer has outstanding properties. Other 1,3-diols may find similar use. Commercially attractive routes to prepare such 1,3-diols are therefore highly desirable.

U.S. Pat. No. 5,304,691 and the art described therein relates to a process for making PDO and HPA (3-hydroxypropanal, a 3-hydroxyaldehyde). In this particular patent, PDO and HPA are made by intimately contacting an oxirane (ethylene oxide, hereinafter 'EO'), a ditertiary phosphine-modified cobalt carbonyl catalyst, a ruthenium catalyst promoter, and syngas (carbon monoxide and hydrogen) in an inert reaction solvent at hydroformylation reaction conditions. A PDO yield of up to 86–87 mole % is reported, using a catalyst comprising cobalt ligated with 1,2-bis(9-phosphabicyclononyl)ethane as bidentate ligand, and either triruthenium(0) dodecarbonyl or bis[ruthenium tricarbonyl dichloride] as cocatalyst.

As mentioned, this process typically results in the synthesis of a mixture of HPA and PDO. However, it would be much more attractive to produce PDO in a single step, or in a higher yield, obviously without co-producing impurities that inhibit the use of PDO in the preparation of polymers etc. In order for this process to be particularly successful, recycle of the catalyst without significant deterioration of performance is needed. Surprisingly such a process, and a catalyst suitably used therein has now been found.

SUMMARY OF THE INVENTION

Accordingly the invention provides a process for an improved oxirane hydroformylation catalyst, the improved oxirane hydroformylation catalyst, and a one step process for preparing a 1,3-diol in the presence of such a catalyst where recovery of product is preferably accomplished via phase separation of a diol rich phase from the bulk reaction liquor.

The process for preparing an improved oxirane hydroformylation catalyst involves:

a) forming a complex (A) by contacting a ruthenium(0) compound with a ditertiary phosphine ligand; and b) forming a complex (B) by subjecting complex (A) to a redox reaction with a cobalt(0) carbonyl compound.

The novel oxirane hydroformylation catalyst involves complex (B), which is postulated to be a ruthenium(+1)-phosphine bidentate:cobalt (−1) complex. The characterizing feature of the novel catalyst is that the metal being ligated is ruthenium rather than cobalt as in the '691 US patent referred to above. Indeed, upon analysis of both systems a distinct difference in the catalysts was noted in the IR spectra. The IR spectrum of the catalyst according to the present invention revealed the presence of phosphorus-ruthenium bands at 2107, 2053, and 2040 $cm^{-1}$, which are not present in the IR spectrum of the catalyst according to the invention of the '691 patent.

Finally, the invention also provides a one step process for preparing a 1,3-diol, comprising the reaction of an oxirane with syngas at hydroformylation conditions in an inert solvent in the presence complex (B) as catalyst.

DETAILED DESCRIPTION OF THE INVENTION

Oxiranes of up to 10 carbon atoms, preferably up to 6 carbon atoms, and ethylene oxide in particular may be converted into their corresponding 1,3-diols by the hydroformylation reaction with syngas in the presence of complex (B) as catalyst.

The 3-diols are made by charging the oxirane, catalyst, optional cocatalyst and/or catalyst promoter and reaction solvent to a pressure reactor with the introduction of syngas (a mixture of hydrogen and carbon monoxide, suitably in a molar ratio of 1:1 to 8:1, preferably 2:1 to 6:1) under hydroformylation conditions.

The process of the present invention comprises batch-type processes, continuous processes and mixed forms thereof.

For best results, the process is conducted under conditions of elevated temperature and pressure. Reaction temperatures range from ambient temperature to 150° C., preferably from 50 to 125° C., and most preferably from 60 to 110° C. The reaction pressure (total pressure, or partial pressure if inert gaseous diluents are used) is desirably in the range from 5 to 15 MPa, preferably from 8 to 10 MPa. In a batch process, the reaction will generally be complete within 1.5 to 5 hours. The reaction solvent is preferably inert, meaning that it is not consumed during the course of the reaction. Ideal solvents for the invention process will solubilize the feed and products during the course of the reaction, but allow phase separation at reduced temperatures. Suitable solvents are described in U.S. Pat. No. 5,304,691 incorporated herewith by reference. For instance, good results may be achieved with ethers, including cyclic and acyclic ethers, optionally in combination with an alcohol or aromatic hydrocarbon. Excellent results have been achieved with methyl tert butyl ether (MTBE) and a mixture of toluene with chlorobenzene.

The process of the present invention, in respect of the preferred embodiment on the synthesis of PDO, can be conveniently described as follows. Separate, combined or staged streams of EO, syngas and catalyst are charged to a reaction vessel, which can be a pressure reaction vessel such as a bubble column or a stirred autoclave, operated batchwise or in a continuous manner.

The components of the feed streams are contacted in a suitable reaction solvent in the presence of the catalyst of the present invention. The EO will preferably be maintained throughout the reaction in a concentration not less than about 0.2% by weight, generally within the range of 0.2 to 20% by weight, preferably 1 to 10% by weight, based on the total weight of the reaction mixture. The process of the invention can be carried out in a continuous mode, whilst maintaining said EO concentration, by for instance staged EO addition.

At the conclusion of the hydroformylation reaction, the product mixture is recovered by conventional methods such as selective extraction, fractional distillation, phase separation, selective crystallization and the like. The unreacted starting materials as well as the catalyst and reaction solvent may, and preferably are recycled for further use.

In a preferred manner of running the process, reaction conditions such as oxirane concentration, catalyst concentration, solvent, product concentration, reaction temperature and the like are selected such as to achieve a homogeneous reaction mixture at elevated temperatures and cause a partitioning of the reaction mixture into an upper solvent phase containing much of the catalyst and a lower phase containing most of the 1,3-propanediol upon cooling the mixture. Such a partitioning facilitates isolation and recovery of product, recyle of catalyst and removal of heavy ends from the solvent system. This process is referred to as a phase separation catalyst recycle/product recovery method.

In this process, the reactor contents are allowed to settle or are transferred to a suitable vessel at or near reaction pressure where upon slight or considerable cooling distinct phases may form that are substantially different, being considerably rich in product or in catalyst and solvent. The phase rich in catalyst and solvent is directly recycled for further reaction with feed materials. Product is recovered from the product rich phase by conventional methods.

It is essential that the reaction is run such that product diol maintains concentration levels in the reaction mix suitable for phase separation. For example, concentration of 1,3-propanediol can be between less than 1 and greater than 50% by weight, generally between 8 and 32% by weight and preferably between 16 and 20% w. Temperature during quiescent settling of phases can be between just above the freezing point of the reaction mixture up to at least 150° C. and very likely higher, generally between 27 and 97° C., and preferably between 37 and 47° C. The EO concentration is maintained to avoid the formation of light alcohols and aldehydes that are miscibilizing agents. Oxiranes will preferably be maintained throughout the reaction in a concentration not less than about 0.2% by weight, generally within the range of 0.2 to 20% by weight, preferably 1 to 10% by weight, based on the total weight of the reaction. The reaction can be run with a two-phase system. However, yields and selectivities are maximized when high concentrations of product are present in a single phase reaction and subsequent phase separation occurs upon cooling.

Partitioning of the reaction mixture can be promoted by the addition of a phase-split inducing agent. Suitable agents include glycols such as ethylene glycol and linear alkanes such as dodecane. Such an agent will be added to the reaction mixture in an amount within the range of about 2 to 10% w, preferably 4 to 8% w based on the total reaction mixture. Alternate methods include addition of 1,3-propanediol into the reaction mixture to bring product concentration up to the target proportion. Also, miscibilizing alcohols and agents with similar polarity such as ethanol, propanol and isopropanol can be added initially, then removed prior to, and subsequently inducing the phase separation.

It is essential in the above described process that as catalyst a complex (B) is used. Complex (B) is believed to comprise a novel class of ruthenium-modified catalysts. The characterizing feature of this novel class involves an oxidized ruthenium metal that is ligated by a tertiary diphosphine ligand, with a cobalt compound as counter ion that may be but preferably is not ligated by a phosphorus ligand.

One compound of this complex comprises the phosphorus ligand. As mentioned, this ligand is a tertiary diphosphine of the general formula:

RRP-Q-PR'R' wherein each group R and R' independently or jointly is a hydrocarbon moiety of up to 30 carbon atoms, and Q is an organic bridging group of 2 to 4 atoms in length. The group R or R', when monovalent, may be alkyl, cycloalkyl, bicycloalkyl or aryl, and preferably of up to 20 carbon atoms, more preferably of up to 12 carbon atoms. Alkyl and/or cycloalkyl groups are preferred. The group Q is preferably composed of carbon atoms, which may form part of a ringsystem such as a benzene ring or a cyclohexane ring. More preferably Q is an alkylene group of 2, 3 or 4 carbon atoms in length, most preferably of 2 carbon atoms in length. A non-limiting list of illustrative diphosphines of this class include 1,2-bis(dimethylphosphino)ethane; 1,2-bis(diethylphosphino)ethane; 1,2-bis(diisobutylphosphino)ethane; 1,2-bis(dicyclohexylphosphino)ethane; 1,2-bis(2,4,4-trimethylpentylphosphino)ethane; 1,2-bis(diethylphosphino)propane; 1,3-bis(diethylphosphino)propane; 1-(diethylphosphino)-3-(dibutylphosphino)propane, 1,2-bis(diphenylphosphino)ethane; 1,2-bis(dicyclohexylphosphino)ethane; 1,2-bis(2-pyridyl, phenylphosphanyl)benzene; 1,2-bis(dicyclopenty-phosphino)ethane; 1,3-bis(2,4,4-trimethylpentyphosphino)propane; 1,2-bis(diphenyl-phosphino) benzene, and the like. These groups R and R' may be substituted with non-hydrocarbon groups themselves. Both groups R and/or both groups R' may also form a ring with the phosphorus atom(s), such as a phosphacycloalkane of from 5 to 8 atoms. Examples on 5-ring systems (phospholano-based ligands) include 1,2-bis(phospholano)ethane, 1,2-bis(2,5-dimethylphospholano) benzene, optically pure (R,R), (R,S), (S,S) 1,2-bis(2,5-dimethylphospholano)ethane or its racemic mixture, and the like. The ring itself may be part of a multiring system. Examples of such ring systems may be found in the aforementioned '691 patent and in WO-A-9842717 (herewith incorporated by reference). In the former phosphabicyclononyl groups are described, in the latter adamantyl-like groups and phosphatrioxatricyclodecyl groups in particular are described. Diphosphines wherein both groups R and R' form a ring with the phosphorus atom are preferred. The most preferred ligands are 1,2-P,P'-bis(9-phosphabicyclo [3.3.1] and/or [4.2.1]nonyl) ethane (hereinafter B9PBN-2), its 1,2-P,P'-propane and/or its 1,3-P,P'-propane analogue (hereinafter B9PBN-3).

Ditertiary phosphine ligands are commercially available. Catalysts prepared therefrom are known in the art and their method of preparation are described in detail in U.S. Pat. Nos. 3,401,204 and 3,527,818, which are both incorporated by reference herein. The phosphine ligands may also be partially oxidized to phosphine oxides in the manner described in the '691 patent.

The ratio of ligand to ruthenium atom may vary from 2:1 to 1:2, preferably from 3:2 to 2:3, more preferably from 5:4 to 4:5 and is most preferably about 1:1. It is hypothesized that this results in a tertiary diphospine ruthenium tricarbonyl compound, but it might also be a bis(tertiary diphosphine ruthenium) pentacarbonyl compound. Unligated ruthenium carbonyl is believed to be an inactive species, and the catalyst preparation therefore seeks to ligate each ruthenium atom.

The counter ion, for best results, is believed to be cobalt tetracarbonyl ($[Co(CO)_4]^-$), although the ion in the active catalyst may be a modification thereof. Part of the cobalt compound may be modified with (excess) tertiary diphosphine, e.g., up to 75 mole %, say up to 50 mole % or less. However, the counter ion is preferably the non-ligated cobalt tetracarbonyl mentioned before. Cobalt carbonyls can be generated by reaction of a starting cobalt source such as cobalt hydroxide with syngas, as described in J. Falbe, "Carbon Monoxide in Organic Synthesis", Springer-Verlag, N.Y. (1970), or otherwise.

The oxidation state of the ruthenium atom is not entirely certain (in theory, ruthenium may have a valence of 0 to 8), which may even change during the course of the hydroformylation reaction. Accordingly, the molar ratio of ruthenium to cobalt may vary within relatively broad ranges. Sufficient cobalt (0) should be added to completely oxidize all of the complexed ruthenium employed. An excess of coblat can be added, but is not of particular value. Suitably, the molar ratio varies from 4:1 to 1:4, preferably from 2:1 to 1:3, more preferably from 1:1 to 1:2.

The catalyst, complex (B), may be made as follows hereafter. The first step in the catalyst preparation is the synthesis of complex (A). This may be done by bringing a suitable Ru(0) source, e.g., triruthenium dodecacarbonyl, in contact with the tertiary diphosphine. Alternatively, the triruthenium dodecacarbonyl may be replaced with less expensive ruthenium sources that in-situ form Ru(0), such as ruthenium(IV) oxide, hydrate.

The conditions at which these compounds are allowed to form a complex are not critical. Temperature and pressure may vary within the ranges already mentioned in respect of the hydroformylation reaction. Syngas may be used as gas cap during the complex formation. On the other hand, it is preferable to use a solvent, preferably the solvent (if any) used in the hydroformylation reaction. Obviously, this solvent should be capable to dissolve the active catalyst, without affecting its properties. Suitable solvents include the ethers described before, and methyl tertiary-butyl ether (MTBE) in particular.

The complex (A) may for instance be made by reacting triruthenium dodecacarbonyl with a stoichiometric amount of a selected ligand in a solvent at a temperature within the range of 90 to 130° C., suitably 100 to 110° C. under a carbon monoxide atmosphere, for a 1 to 3 hours (i.e., until completion).

Next, the complex (A) is brought in contact with a suitable cobalt compound, again at the aforementioned (non critical) conditions. A suitable cobalt source is dicobalt octacarbonly, but other cobalt(0) complexes, preferably with the exception of phosphine-modified complexes, may be used as well. For instance, the selected cobalt carbonyl, and optional promoters, if any, are added to the solution which is then maintained at the elevated temperature for a time of about 15 to 60 minutes. This process is referred to as a step-wise preparation method.

Suitable cobalt sources also include salts which are reduced to the zero valence state by heat-treatment e.g. in an atmosphere of hydrogen and carbon monoxide. Examples of such salts comprise, for instance, cobalt carboxylates such as acetates, octanoates, etc., which are preferred, as well as cobalt salts of mineral acids such as chlorides, fluorides, sulfates, sulfonates, etc. Operable also are mixtures of these cobalt salts. It is preferred, however, that when mixtures are used, at least one component of the mixture be cobalt alkanoate of 6 to 12 carbon atoms. The reduction may be performed prior to the use of the catalysts or it may be accomplished simultaneously with the hydroformylation process in the hydroformylation zone.

It is also within the scope of the present invention to prepare complex (A) by a self-assembly method, wherein all catalyst components are brought together at the same time, but the conditions and in particular the solvent, are selected such as to favor the formation of a ligated ruthenium species, rather than a ligated cobalt species. The presence of the Ru-ligated species rather than the Co-phosphine species may be confirmed by e.g. IR analysis.

In this respect it is emphasized that in the aforementioned U.S. Pat. No. 5,304,691 it was said that the form of the ruthenium is not critical. Although it is suggested to use ruthenium complexes of phosphines described in this reference, any such use is clearly to prepare tertiary phosphine-complexed cobalt carbonyl catalysts, with consequently the loss of the phosphine-complexed ruthenium starting material.

The optimum ratio of oxirane feed to complex (B) will in part depend upon the particular complex employed. However, molar ratios of oxirane to the cobalt within complex (B) from 2:1 to 10,000:1 are generally satisfactory, with molar ratios of from 50:1 to 500:1 being preferred.

Promoters, such as described in the aforementioned '691 patent may be used. The currently preferred promoter, because of its availability and demonstrated promotion of EO conversion are dimethyldodecylamine and triethylamine.

Commercial operation will require efficient catalyst recovery with multiple cycles of essentially complete recycle of catalyst to the reaction. The preferred catalyst recovery process involves separation of the two liquid phase mixture noted previously and recycle of the bulk solvent phase to the reactor and return therewith of at least 60 to 90% by weight of the starting catalyst.

The invention is further illustrated by the following examples.

TABLE 1

| | | Materials and formulations |
|---|---|---|
| Co source | CoOc | Cobalt octoate |
| | DCO | Dicobalt octacarbonyl |
| Ru source | TRC | Triruthenium dodecacarbonyl |
| | BRCC | Bis(ruthenium tricarbonylchloride) |
| Ligand | B9PBN-2 | 1,2-P,P'-bis(9-phosphabicyclononyl)ethane |
| | BDEPE | 1,2-bis(diethylphosphino)ethane |
| | BDIPE | 1,2-bis(diiosbutylphosphino)ethane |
| | BDOPE | 1,2-bis(2,4,4-trimethylpentylphosphino)ethane |
| | BDMPE | (R,R) 1,2-bis(dimethylphospholano)ethane |
| Solvent | MTBE | Methyl-t-butyl ether |
| | T/CB | 5:1 v/v mixture of toluene/chlorohenzene |
| Oxirane | EO | Ethylene oxide |
| Promoter | DMDA | Dimethyldodecylamine |
| | NaAc | Sodium acetate |

The IR analysis was conducted with in situ cylindrical internal reflectance reactors of the type described by W. R. Moser, J. E. Cnossen, A. W. Wang, and S. A. Krouse in *Journal of Catalysis*, 1985, 95, 21; sold by Spectra-Tech Inc. mated to a Nicolet Magna 550 spectrometer. The spectral region of interest includes both the catalyst bands and aldehyde intermediates in the region of 1500 to 2500 $cm^{-1}$.

EXAMPLE 1

Preparation of Complex (B)

In a dry box the following materials were loaded into a 50 ml stainless steel reactor fitted with optics for in-situ reaction monitoring by mid IR analysis: 61 mg TRC (0.286 mmoles Ru), 171 mg B9PBN-2 (0.551 mmoles) and 17 ml of MTBE.

The reactor was sealed, removed from the dry box, placed into the optical bench of an IR spectrometer, and pressurized to 2.2 MPa with carbon monoxide. The reactor was heated to 105° C. and the progress of the complex (A), formation was monitored by IR. Once the temperature reached 105° C., hydrogen was added to bring the gas composition to an approximate 3:1 syngas ratio.

To this mixture was added a solution of 113 mg DCO and 47 mg of DMDA dissolved in 5 ml of MTBE, using excess 1:1 syngas pressure to bring the total reactor pressure to 8.6 MPa. After an additional 35 minutes at 105° C. the reactor was cooled.

Comparative Example A

Preparation of a Ligated Co Catalyst as in U.S. Pat. No. 5,304,691

In a dry box the following materials were loaded into a 50 ml stainless steal reactor fitted with optics for in-situ reaction monitoring by mid IR analysis: 228 mg CoOc (0.66 mmoles Co), 74 mg BRCC (0.289 mmoles Ru), 222 mg B9PBN-2 (0.715 mmoles), 18 mg sodium acetate (0.22 mmoles) and 23 ml T/CB.

The reactor was sealed, removed from the dry box, placed into the optical bench of an IR spectrometer, and pressurized to 9.0 MPa with 4:1 syngas. The reactor was heated to 130° C. and the progress of the catalyst formation was monitored by IR.

EXAMPLE 2

Preparation of Complex (B) by Self-Assembly

To a 100 ml autoclave was charged in a manner similar to Comparative Example A: 228 mg CoOc (0.66 mmole); 23 ml MTBE; 62 mg TRC (0.29 mmole); 167 mg B9PBN-2 (0.50 mmole); and 17 mg NaAc (0.21 mmole). Again the progress of the catalyst formation was monitored by IR.

Catalyst Analysis by IR

Upon addition of B9PBN-2 to TRC, the TRC bands at 2059, 2029 and 2009 $cm^{-1}$ disappeared and an increase was noticed in bands at 1954, 1884 and 1853 $cm^{-1}$. Upon addition of cobalt carbonyl the oxidation of chelated ruthenium took place accompanied by an instantaneous shift in the IR bands, generating characteristic bands at 2040, 2053, and 2107 $cm^{-1}$ as well as a band at 1890 $cm^{-2}$ that is characteristic for the (unligated) cobalt carbonyl anion.

Figure 1:
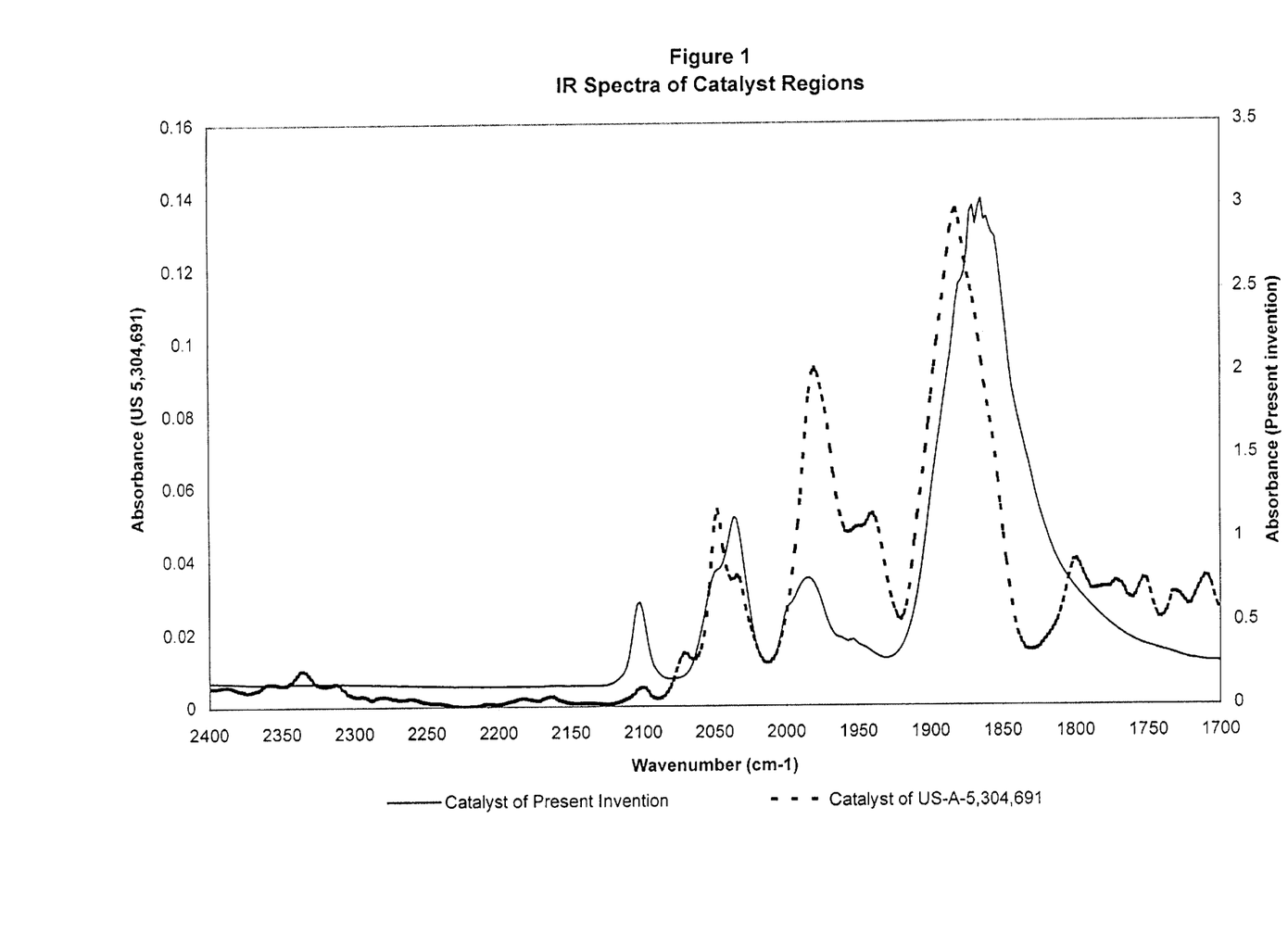
FIG. 1 is a comparison of the in-situ IR spectrum of the invention catalyst (as prepared) with the in-situ IR spectrum of a comparison catalyst (as prepared).

Referring to FIG. 1, the solid line is an in-situ IR spectrum of the complex (B) prepared as described in Example 1. The predominant catalysts bands (at 2040, 2053, and 2107 $cm^{-1}$) are characteristic of phosphine-modified ruthenium compounds. The dotted line is an in-situ IR spectrum of the comparative catalyst. The in-situ IR spectrum of the complex (B) prepared by the self-assembly method closely corresponded to that of the catalyst made in Example 1.

EXAMPLE 3

Preparation of PDO

At 80° C. 1.1 g EO was added to the reaction mixture of Example 1, using excess 1:1 syngas pressure. Syngas (1:1) was added as needed to the reaction mixture to maintain the reaction pressure between 10.4 and 11.1 MPa. The EO was allowed to react completely. When cooled, the reactor was opened and a two-phase liquid was isolated. GC analysis revealed the primary EO-derived product in both phases was PDO. (Yield of greater than 50 mole %) In a similar manner, the catalyst of comparative example A was used. However, the two-phase liquid isolated at the end of this experiment was found to comprise a lower phase showing an approximately 50/50 mixture of PDO and HPA and an upper phase containing PDO, HPA and other materials. (Yield of greater then 50 mole %)

The progress of both reactions were tracked by IR, observing the intensity of absorbance of the intermediate 3-hydroxypropionaldehyde carbonyl band (1728 $cm^{-1}$). The results are reproduced FIG. 2.

Figure 2:
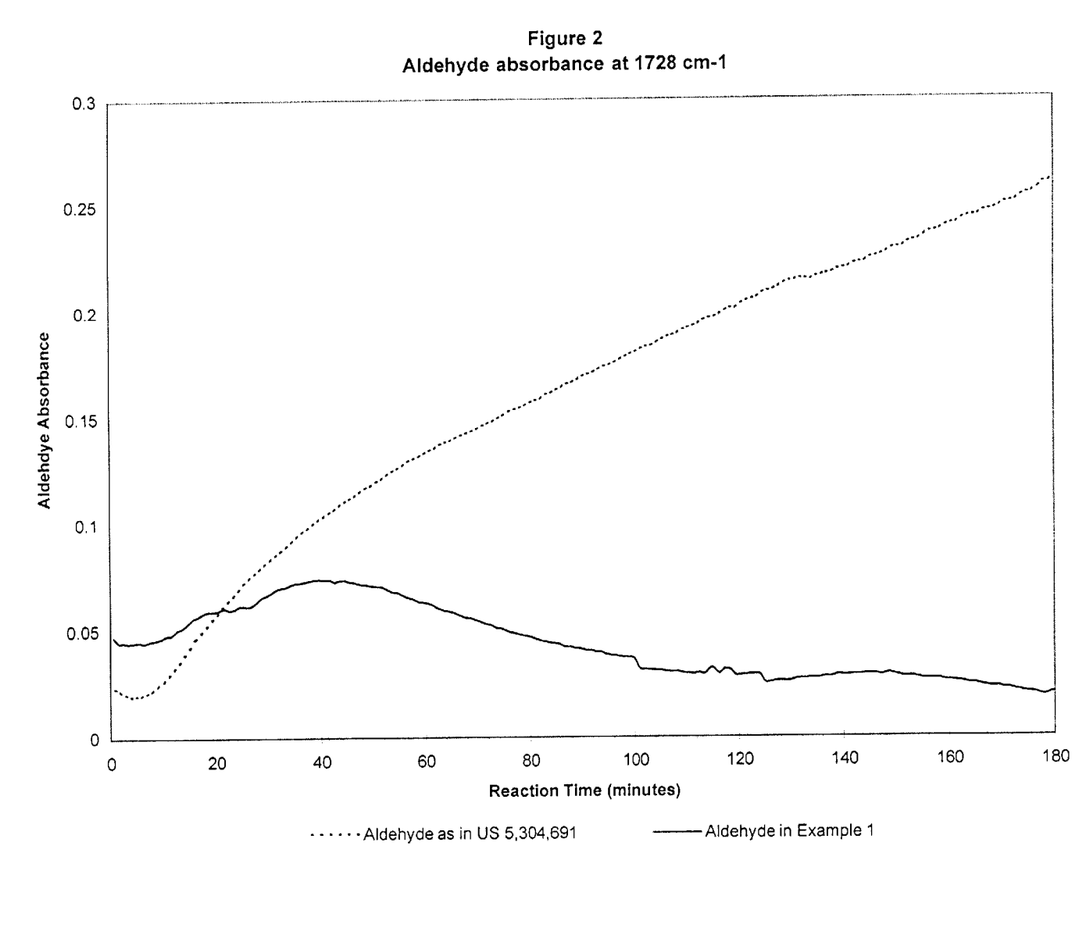
FIG. 2 is a comparison of the in-situ IR spectrum of the HPA absorbance at 1728 $cm^{-1}$ over the course of the reaction using a catalyst in accordance with the present invention, as compared to the comparison catalyst.

Using the catalyst of the present invention, the aldehyde band was seen to rise only slightly at the onset of reaction and then decrease rapidly as the HPA was converted into PDO. Said band increased steadily over the course of the reaction when the catalyst of comparative example A was used. Indicating the superior hydrogenating ability of the catalyst of the present invention.

Comparative Example B

The experiment of Example 3, using the catalyst of Comparative example A was essentially followed, with staged addition of EO (4 steps). In about 4 to 6 hours 1,3-PDO was prepared in a yield of 66 mole % at 80% selectivity. Next, the crude liquid product was fractionally distilled under vacuum (<0.1 kPa) to recover PDO as distillate product fraction. The remainder was recycled with additional EO and syngas, plus make-up solvent for a second run. The PDO yield was found to be only 44 mole %, with only 67% selectivity. When the remainder of this product was recycled and allowed to catalyze a third run, the PDO yield had essentially vanished (2 mole %).

EXAMPLE 4

The experiment of Example 3, using a catalyst corresponding to that of Example 1, however using BDEPE instead was essentially followed, with staged addition of EO (4 steps). In about 4 to 6 hours PDO was prepared in a yield of 48 mole % at 57% selectivity. Next, the crude liquid product was fractionally distilled under vacuum (<0.1 kPa) to recover PDO as distillate product fraction. The remainder was recycled with additional EO and syngas, plus make-up solvent for a second run. The PDO yield was found to be 40 mole %, with 54% selectivity. When the catalyst was recycled and allowed to catalyze the reaction in this manner for the tenth time, the PDO yield was still found to be 49 mole %, with 59% selectivity.

No apparent loss of catalyst activity was noticed over 12 EO additions. Furthermore, P-NMR of the final product solution indicated no free BDEPE, with most of the P-ligand still bound to the ruthenium. It may therefore be concluded that the novel catalysts of the present invention possess increased stability.

EXAMPLE 5

Various (scouting) experiments similar to that of Example 3 were conducted, using a catalyst prepared by self assembly with an initial Co:Ru:ligand molar ratio of 2:1:2. The test results are described in the following Table.

TABLE 2

| Ligand | PDO Yield (mole %) | PDO Selectivity (%) |
|---|---|---|
| BDEPE | 48–73 | 83–87 |
| BDIPE | 36–53 | 80–86 |
| BDOPE | 31 | 69 |
| BDMPE | 51–71 | 78–95 |

From these results it may be concluded that the catalysts of the present invention are invariably suitable for the one-step conversion of oxiranes.

EXAMPLE 6

Preparation of Complex (B)

In a dry box the following materials were loaded into a 50 ml stainless steel reactor fitted with zinc sulfide optics for in-situ reaction monitoring by mid IR analysis: 128 mg TRC (0.600 mmoles Ru), 186 mg B9PBN-2 (0.600 mmoles), 9 ml of toluene and 9 ml of MTBE.

Figure 3:
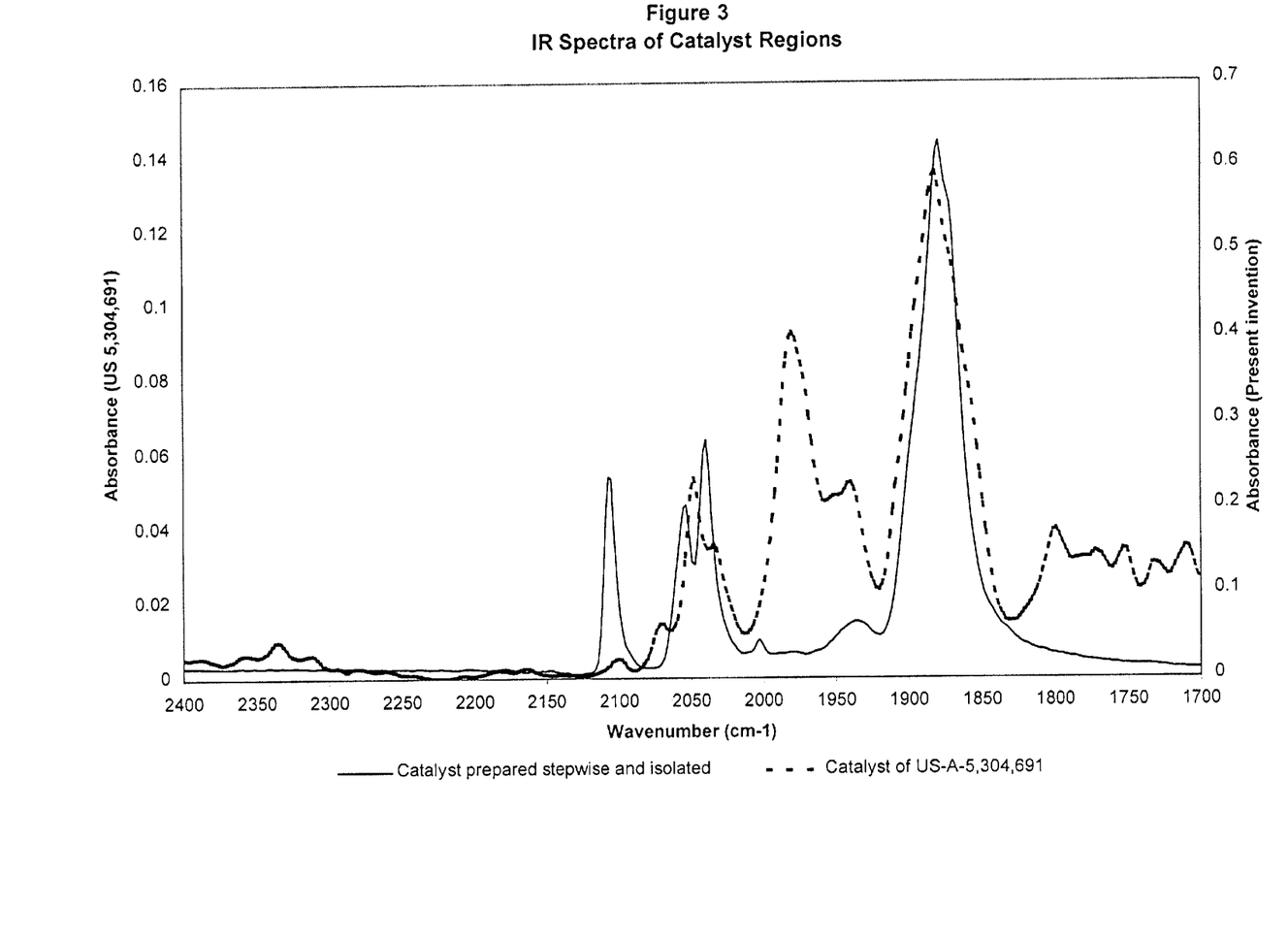
FIG. 3 is an IR spectrum of catalyst regions of the isolated solid of example 5.

The reactor was sealed, removed from the dry box, placed into the optical bench of an IR spectrometer, and pressurized to 1.7 MPa with carbon monoxide. The reactor was heated to 105° C. and the progress of the complex (A) formation was monitored by IR. Upon heating the TRC bands at 2059, 2029 and 2009 cm−1 disappeared and an increase was noticed in bands at 1954, 1882 and 1861 cm−1. After one hour at 105° C., hydrogen was added to bring the gas composition to an approximate 3:1 syngas ratio, 8.29 MPa, and a solution of 105 mg DCO (0.614 mmoles Co) dissolved in 6 ml of MTBE was added via excess syn gas pressure, bringing the total reactor pressure to 10.3 MPa. Upon addition of cobalt carbonyl, the oxidation of chelated ruthenium took place accompanied by an instantaneous shift in the IR bands generating characteristic bands at 2040, 2053, and 2107 cm−1 as well as a band at 1890 cm−1 that is characteristic for the (unligated) cobalt carbonyl anion. This was held at 105° C. for 1.5 hours without apparent change in the catalyst composition. Upon heating to 130° C., the mid IR spectrum indicated no alteration in the catalyst composition. The reactor was cooled to room temperature, opened and 0.25 grams of yellow-orange catalyst solids were isolated by suction filtration and dried in vacuo. An infrared spectrum of the isolated solid is shown in FIG. 3, the only bands metal carbonyl bands present are due to phosphine ligated ruthenium (I) with a cobalt (−I) tetracarbonyl anion. No other cobalt carbonyls are present. This complex is identical to catalyst solids isolated from a one step 1,3-propanediol reaction of the present invention.

EXAMPLE 7

Use of Isolated Complex (B) for Preparation of 1.3-propanediol in a Single Step In a dry box 0.24 grams of catalyst solids from Example 5 and 23 ml of MTBE were loaded into a 50 ml stainless steal reactor fitted with zinc sulfide optics for in-situ reaction monitoring by mid IR analysis. The reactor was sealed, removed from the dry box, placed into the optical bench of an IR spectrometer, and pressurized to 7.0 MPa with 4:1; hydrogen:carbon monoxide. The reactor was heated to 90° C. and 1.9 grams of EO was added to the reaction mixture using excess 1:1 synthesis gas pressure. The 1:1 synthesis gas was added to the reaction mixture to maintain a reactor pressure between 10.1 and 10.8 MPa. Within an hour the first aliquot of ethylene oxide was consumed and a second 1.9 grams (3.8 grams total) of ethylene oxide was injected into the reactor. The reaction mixture again rapidly consumed synthesis gas, make up gas being added as needed. The reaction was run to essentially complete EO consumption during the entire reaction, the IR spectrum of the catalyst region remains the same as the starting catalyst solids. Upon cooling and opening the reactor a two phase mixture was obtained. GC analysis of both phases revealed a PDO yield in excess of 50% with only trace amounts of HPA detected.

EXAMPLE 8

Phase Separation Catalyst Recycle/Product Recovery Process with Catalyst formed by Self Assembly In an inert atmosphere drybox, to a 300 ml autoclave, 1.85 grams (5.35 mmole Co) cobalt(II) ethylhexanoate, 1.392 grams (4.48 mmole) 1,2-bis(9-phosphacyclononyl) ethane, 0.509 grams (2.3 mmole Ru) triruthenium dodecylcarbonyl, 145.85 grams methyl-tert-butyl ether (MTBE) and 0.30 grams dimethyldodecyl amine was added. The autoclave body was sealed and fitted to a benchscale process unit. Under a headspace of 4:1 $H_2$:Co ratio syngas at 1500 psig the mixture was allowed to reach equilibrium and preform catalyst over 2 hours at 130° C. Reactor temperature was reduced to 90° C. An addition of 16.96 grams of ethylene oxide (EO) was made and allowed to react with syngas feed at a 2:1 $H_2$:CO ratio until the EO is substantially but not completely consumed. The reactor content was transferred under reaction conditions to a phase separation vessel where phase separation began immediately. From the vessel, 12.94 grams lower layer material was isolated. The upper layer reaction liquor was recycled back to the reactor. Compositions of the upper and lower layer are given in Table 3. Catalyst partition data is shown in Table 4. The product, 1,3-propanediol, was produced at an average rate of 20 g/L/hr.

EXAMPLE 9

Phase Separation Process, Recycle 1

The recycled reaction liquor from example 8 was heated to 90° C. An addition of 14.74 grams ethylene oxide was made and allowed to react under a head space of 2:1 $H_2$:CO ratio syngas at 1500 psig until the EO was substantially consumed. The reactor contents were transferred under syngas pressure to a phase separation vessel where phase separation began immediately resulting in the isolation of 8.22 grams of lower layer material. Upper layer reaction liquor was recycled back to the reactor. Compositions of the upper and lower layer are given in Table 3. Catalyst partition data is shown in Table 4. The averaged reaction rate through this recycle gave 14 g/L/hr.

EXAMPLE 10

Phase Separation Process, Recycle 2

The recycled reaction liquor from example 9 was heated to 90° C. An addition of 14.74 grams ethylene oxide was made and allowed to react under a head space of 2:1 $H_2$:CO ratio syngas at 1500 psig. The reactor contents were transferred under syngas pressure to a phase separation vessel where phase separation began immediately and 8.50 grams of lower layer material was isolated. Upper layer reaction liquor was recycled back to the reactor. Compositions of the upper and lower layer are given in Table 3 Catalyst partition data is shown in Table 4. The averaged reaction rate through this recycle gave 37 g/L/hr.

EXAMPLE 11

Phase Separation Process, Recycle 3

The recycled reaction liquor from example 10 was heated to 90° C. An addition of 14.74 grams ethylene oxide was made and allowed to react under a head space of 2:1 $H_2$:CO ratio syngas at 1500 psig. The reactor contents were, transferred under syngas pressure to a phase separation vessel where phase separation began immediately and 19.50 grams of lower layer material was isolated. Upper layer reaction liquor was recycled back to the reactor. Compositions of the upper and lower layer are given in Table 3. Catalyst partition data is shown in Table 4. The averaged reaction rate through this recycle gave 49 g/L/hr.

EXAMPLE 12

Phase Separation Process, Recycle 4

The recycled reaction liquor from example 11 was heated to 90° C. An addition of 14.74 grams ethylene oxide was made and allowed to react under a head space of 2:1 $H_2$:CO ratio syngas at 1500 psig. The reactor contents were transferred under syngas pressure to a phase separation vessel where separation began immediately and 32.80 grams of lower layer material was isolated. Upper layer reaction liquor was recycled back to the reactor. Compositions of the upper and lower layer are given in Table 3. Catalyst partition data is shown in Table 4. The averaged reaction rate through this recycle gave 34 g/L/hr.

EXAMPLE 13

Phase Separation Process, Recycle 5

The recycled reaction liquor from example 12 was heated to 90° C. An addition of 14.74 grams ethylene oxide was made and allowed to react under a head space of 2:1 $H_2$:CO ratio syngas at 1500 psig. The reactor contents were transferred under syngas pressure to a phase separation vessel where phase separtion began immediately and 71.90 grams of lower layer material was isolated. Upper layer reaction liquor was recycled back to the reactor. Compositions of the upper and lower layer are given in Table 3. Catalyst partition data is shown in Table 4. The averaged reaction rate through this recycle gave 30 g/L/hr.

The three most important results for the phase separation are: 1) achieve an acceptable high enough rate of production of PDO, 2) recycle most of the catalyst (in the upper phase), and 3) recover concentrated product (PDO) in the lower phase.

The data on rate of production of PDO in the examples above shows that an acceptable rate of reaction is achieved and that the catalyst is active after 5 recycles (#1).

Table 4 shows that a high percentage of the catalyst is directly recycled in the upper phase (#2).

Table 3 shows high recovery of PDO in the lower phase (#3).

TABLE 3

Phase Split Primary Compositions

| Example | Layer | PDO % w | MTBE % w | Mass (g) |
|---|---|---|---|---|
| 8 | Lower | 59.70 | 18.13 | 12.94 |
| 9 | Lower | 47.97 | 16.60 | 8.22 |
| 10 | Lower | 45.97 | 19.15 | 8.50 |
| 11 | Lower | 47.32 | 21.73 | 19.50 |
| 12 | Lower | 45.16 | 20.99 | 32.80 |
| 13 | Lower | 47.50 | 25.78 | 71.90 |
| 8 | Upper | 4.74 | 85.70 | 152.36 |
| 9 | Upper | 5.15 | 87.16 | 160.04 |
| 10 | Upper | 17.67 | 77.60 | 167.19 |
| 11 | Upper | 27.31 | 54.86 | 163.47 |
| 12 | Upper | 14.41 | 69.85 | 147.04 |
| 13 | Upper | 10.59 | 80.36 | 93.46 |

TABLE 4

Catalyst Species Partition Data

| Example | Layer | % of Available Catalyst (Co ; Ru) |
|---|---|---|
| 8 | Upper | 90 ; 88 |
| 9 | Upper | 91 ; 88 |
| 10 | Upper | 93 ; 91 |
| 11 | Upper | 82 ; 75 |
| 12 | Upper | 78 ; 71 |
| 13 | Upper | 61 ; 75 |
| 8 | Lower | 10 ; 12 |
| 9 | Lower | 9 ; 12 |
| 10 | Lower | 7 ; 9 |
| 11 | Lower | 18 ; 25 |
| 12 | Lower | 21 ; 29 |
| 13 | Lower | 38 ; 25 |

EXAMPLE 14

Phase Separation Catalyst Recycle/Product Recovery Process with Catalyst Prepared via Stepwise Procedure In an inert atmosphere drybox, to a 300 ml autoclave, 2.14 grams (6.90 mmole) 1,2-bis(9-phosphacyclononyl) ethane, 0.694 grams (3.25 mmole Ru) triruthenium dodecylcarbonyl, 119 grams methyl tert-butyl ether (MTBE) was added. The autoclave body was sealed and fitted to a benchscale process unit. Under a headspace of 4:1 ($H_2$:CO) syngas at 1500 psig the mixture was allowed to reach equilibrium over 1 hour at 105C. To the reactor a solution of, 1.11 grams (6.50 mmole Co) dicobalt octacarbonyl and 0.108 grams (1.32 mmole) sodium acetate in 33.3 grams MTBE was added at reaction conditions. The catalyst was allowed to preform at 105° C. and 1500 psig for 1.75 hours. Reactor temperature was reduced to 90° C. Two separate additions totaling 13.2 grams of ethylene oxide (EO) were made and allowed to react with a 2:1 ($H_2$:CO) syngas feed until sustantially all of the EO was consumed. The reactor contents were transferred under syngas pressure to a temperature controlled phase separation vessel. The phase separation was allowed to equilibrate at 43° C. A lower phase of 36.8 grams was isolated. Upper phase was recycled back to the reactor. Compositions of the upper and lower phase are given in Table 5. Catalyst partition data is shown in Table 6. The product, 1,3-propanediol was produced at an average rate of 26 g/L/hr.

EXAMPLE 15

Phase Separation Process, Recycle 1

The recycled reaction liquor from example 14 was heated to 90° C. An addition of 14.74 grams ethylene oxide was made and allowed to react under a head space of 2:1 syngas at 1500 psig. The reactor content was transferred under syngas pressure to a phase separation vessel. When equilibrated to 43° C., 28.5 grams of lower phase material was isolated. Upper phase reaction liquor was recycled back to the reactor. Compositions of the upper and lower phase are given in Table 5. Catalyst partition data is shown in Table 6. The averaged reaction rate through this recycle gave 24 g/L/hr.

EXAMPLE 16

Phase Separation Process, Recycle 2

The recycled reaction liquor from example 15 was heated to 90° C. An addition of 11.00 grams ethylene oxide was made and allowed to react under a head space of 2:1 syngas at 1500 psig. The reactor content was transferred under syngas pressure to a phase separation vessel. When equilibrated to 43° C., 24.8 grams of lower phase material was isolated. Upper phase reaction liquor was recycled back to the reactor. Compositions of the upper and lower phase are given in Table 5. Catalyst partition data is shown in Table 6. The averaged reaction rate through this recycle gave 35 g/L/hr.

EXAMPLE 17

Phase Separation Process, Recycle 3

The recycled reaction liquor from example 16 was heated to 90° C. An addition of 11.00 grams ethylene oxide was made and allowed to react under a head space of 2:1 syngas at 1500 psig. The reactor contents were transferred under syngas pressure to a phase separation vessel. When equilibrated to 43° C., 19.1 grams of lower phase material was isolated. Upper phase reaction liquor was recycled back to the reactor. Compositions of the upper and lower phase are given in Table 5. Catalyst partition data is shown in Table 6. The averaged reaction rate through this recycle gave 23 g/L/hr.

EXAMPLE 18

Phase Separation Process, Recycle 4

The recycled reaction liquor from example 17 was heated to 90° C. An addition of 11.00 grams ethylene oxide was made and allowed to react under a head space of 2:1 syngas at 1500 psig. The reactor content was transferred under syngas pressure to a phase separation vessel. When equilibrated to 43° C., 38.9 grams of lower phase material was isolated. Upper phase reaction liquor was recycled back to the reactor. Compositions of the upper and lower phase are given in Table 5. Catalyst partition data is shown in Table 6. The averaged reaction rate through this recycle gave 18 g/L/hr.

EXAMPLE 19

Phase Separation Process, Recycle 5

The recycled reaction liquor from example 18 was heated to 90° C. An addition of 11.00 grams ethylene oxide was made and allowed to react under a head space of 2:1 syngas at 1500 psig. The reactor content was transferred under syngas pressure to a phase separation vessel. When equilibrated to 43° C., 38.9 grams of lower phase material was isolated. Upper phase reaction liquor was recycled back to the reactor. Compositions of the upper and lower phase are given in Table 5. Catalyst partition data is shown in Table 6. The averaged reaction rate through this recycle gave 17 g/L/hr.

The data on rate of production of PDO in the examples above shows that an acceptable rate of reaction is achieved and that the catalyst is active after 5 recycles (#1).

Table 6 shows that a high percentage of the catalyst is directly recycled in the upper phase (#2).

Table 5 shows high recovery of PDO in the lower phase (#3).

TABLE 5

Phase Split Primary Compositions

| Example | Layer | PDO % w | MTBE % w | Mass (g) |
| --- | --- | --- | --- | --- |
| 14 | Lower | 63.68 | 16.15 | 24.80 |
| 15 | Lower | 49.68 | 17.39 | 28.50 |
| 16 | Lower | 68.08 | 18.03 | 24.80 |
| 17 | Lower | 53.34 | 24.31 | 19.10 |
| 18 | Lower | 33.32 | 19.39 | 38.90 |
| 19 | Lower | 30.03 | 25.91 | 29.80 |
| 14 | Upper | 7.20 | 44.63 | 165.07 |
| 15 | Upper | 8.89 | 61.35 | 152.73 |
| 16 | Upper | 36.69 | 48.66 | 139.09 |
| 17 | Upper | 16.88 | 54.86 | 131.42 |
| 18 | Upper | 6.14 | 86.65 | 104.92 |
| 19 | Upper | 27.30 | 34.57 | 88.12 |

TABLE 6

Catalyst Species Partition Data

| Example | Layer | % of Available Catalyst (Co ; Ru) |
| --- | --- | --- |
| 14 | Upper | 70 ; 67 |
| 15 | Upper | 82 ; 68 |
| 16 | Upper | 85 ; 72 |
| 17 | Upper | 89 ; 73 |
| 18 | Upper | 67 ; 63 |
| 19 | Upper | 73 ; 73 |
| 14 | Lower | 30 ; 33 |
| 15 | Lower | 18 ; 32 |
| 16 | Lower | 15 ; 28 |
| 17 | Lower | 11 ; 27 |
| 18 | Lower | 33 ; 37 |
| 19 | Lower | 27 ; 27 |

EXAMPLE 20

Recycle of Lower Phase Stepwise Assembled Catalyst

Lower layer samples from examples 14 and 15 rich in 1,3-propanediol product were distilled at 90–110° C. under vacuum conditions of 60–4 mm Hg. Collections of methyl tert-butyl ether solvent and 1,3-propanediol were made on the column overhead. Overhead material was greater than 92% 1–3, propanediol. The distillation was carried out such that 75% of the initial charge mass was distilled. A 10 gram sample of the distillation bottoms containing recycled catalyst, some 1–3,propanediol and minor amounts of heavy ends was inventoried into a 300 ml autoclave in an inert atmosphere drybox. To the autoclave was added 74 grams of fresh methyl tert-butyl ether solvent. The autoclave was sealed and fitted to a benchscale process unit. The catalyst liquor was heated to 90° C. with stirring. Under a headspace of 4:1 ($H_2$:CO) syngas, 11.00 grams of ethylene oxide was added and allowed to react. The reactor contents was transferred under syngas pressure to a phase separation vessel where at 45° C. phase separation began. When equilibrated, 12.6 grams of lower phase material was isolated. This lower phase contained 56.47% 1,3-propanediol product. Upper phase reaction liquor was recycled back to the reactor and heated to 90° C. under a syngas feed headspace of 2:1 ($H_2$:CO). To this recycled solvent phase, 11.00 grams of ethylene oxide was added and allowed to react. The reactor contents were transferred under syngas pressure to a phase separation vessel where at 43° C. phase separation began. When equilibrated, 24.5 grams of lower phase material was isolated. This lower phase contained 45.14% 1,3-propanediol product. These reactions afforded an 81% product yield. This proves that the catalyst is robust and still active even after being distilled from the product phase and recycled twice through the upper phase of subsequent reactions.

EXAMPLE 21

Use of Hexane as Phase Split Inducing Agent

In an inert atmosphere drybox, to a 300 ml autoclave, 1.159 grams (3.73 mmole) 1,2-bis(9-phosphacyclononyl) ethane, 0.696 grams (3.27 mmole Ru) triruthenium dodecylcarbonyl, 119 grams methyl tert-butyl ether (MTBE) was added. The autoclave body was sealed and fitted to a benchscale process unit. Under a headspace of 4:1 ($H_2$:CO) syngas at 1500 psig the mixture was allowed to reach equilibrium over 1.5 hour at 105° C. To the reactor a solution of, 1.13 grams (6.50 mmole Co) dicobalt octacarbonyl and 0.108 grams (1.32 mmole) sodium acetate in 33.3 grams MTBE was added at reaction conditions. The catalyst was allowed to preform at 105° C. and 1500 psig for 1.75 hours. Reactor temperature was reduced to 90° C. One addition of 22 grams of ethylene oxide (EO) was made and allowed to react with a 2:1 ($H_2$:CO) syngas feed. The reactor contents were transferred under syngas pressure to a temperature controlled phase separation vessel. The phase separation was allowed to equilibrate at 43° C. A lower phase of 9.746 grams was isolated. Upper phase was recycled back to the reactor. As in a fashion similar to above examples additional ethylene oxide was added to the recycled upper layer and allowed to react followed by a temperature induced phase split. On the third recycle in this example 11.00 grams of ethylene oxide was added and allowed to react at 90° C. and 1500 psig. Transfer to phase separation vessel and subsequent to cooling to 35° C., no phase separation was apparent. Two separate additions of 11.00 gram aliquots of ethylene oxide followed by reaction at stated conditions, and cooling to 33° C. did not produce a 1,3-propanediol concentration where a phase separation could be made. We believe that this reaction produced some by-products, such as ethanol and propanol, that are miscibilizing in nature that prevented the phase separation. Addition of 10 grams of hexane while in the reactor at stated conditions followed by transfer to the separation vessel and cooling invoked a phase separation at 77° C. This is one way to change the polarity of the system such that a phase split can be induced. It is even possible to add before or during the reaction miscibilizing agents to ensure a single phase reaction. These miscibilizing agents can then be removed, such as by distillation or flashing, to invoke a phase split for product recovery. After equilibrating to 43° C., the a lower layer sample of 92.7 grams was isolated and contained 48% 1,3-propanediol product.

We claim:

1. A hydroformylation catalyst prepared by a process which involves:
    a) forming a complex (A) by contacting a ruthenium(0) compound with a ditertiary phosphine ligand such that the ruthenium(0) compound is ligated by the phosphine ligand; and
    b) forming a complex (B) by subjecting complex (A) to a redox reaction with a cobalt(0) carbonyl compound such that the cobalt(0) carbonyl compound is not ligated by the phosphine ligand.

2. The hydroformylation catalyst of claim 1, characterized by having a cobalt carbonyl anion IR band at 1894 $cm^{-1}$.

3. The catalyst of claim 1 wherein the ditertiary phosphine ligand is of the general formula:
    wherein each group R and R' independently or jointly is a hydrocarbon moiety of up to 30 carbon atoms, and Q is an organic bridging group of 2 to 4 atoms in length.

4. The catalyst of claim 3 wherein group R or R' each independently is an alkyl, cycloalkyl, bicycloalkyl, or aryl group.

5. The catalyst of claim 4 wherein group R or R' each independently has up to 20 carbon atoms.

6. The catalyst of claim 4 wherein group Q is composed of carbon atoms.

7. The catalyst of claim 6 wherein Q is an alkylene group of 2, 3, or 4 carbon atoms in length.

8. The catalyst of claim 3 wherein both groups R and/or R' are part of a bivalent group, forming with a phosphorus atom a phosphacycloalkane of from 5 to 8 atoms, which itself may be part of a multi ring system.

9. The catalyst of claim 3 wherein the ditertiary phosphine ligand is selected from the group consisting of 1,2-bis(dicyclohexylphosphino)ethane, 1,2-bis(diphenylphosphino)ethane, 1,2-bis(diethyl-phosphino)ethane, 1-(diethylphosphino)-3-(dibutylphosphino)propane, 1,2-bis(diphenyl-phosphino)benzene, 1,2-bis(dimethylphosphino)ethane, 1,2-bis(2,4,4-trimethylpentylphosphino)ethane, 1,2-bis(diisobutylphosphino)ethane, 1,2-P,P'-bis(9-phosphabicyclo [3.3.1], and [4.2.1]nonyl)ethane, and its 1,2-P,P'-propane, and 1,3-P,P'-propane analogues.

10. The catalyst of claim 1 wherein the ratio of the ligand to ruthenium atom varies from 2:1 to 1:2.

11. The catalyst of claim 10 wherein the ratio of ligand to ruthenium atom varies from 3:2 to 2:3.

12. The catalyst of claim 1 wherein triruthenium(0) dodecacarbonyl is used.

13. The catalyst of claim 1 wherein dicobalt octacarbonyl is used.

14. The catalyst of claim 1 wherein the molar ratio of ruthenium to cobalt is from 4:1 to 1:4.

15. The catalyst of claim 14 wherein the molar ratio of ruthenium to cobalt is from 2:1 to 1:3.

16. The process of claim 15 wherein the molar ratio of ruthenium to cobalt is from 1:1 to 1:2.

17. The catalyst of claim 14 wherein the complex (B) is made by a step-wise method.

18. The catalyst of claim 17 wherein the ruthenium(0) compound is reacted with the ditertiary phosphine ligand in the presence of syngas.

19. The catalyst of claim 17 wherein the ruthenium(0) compound is reacted with the ditertiary phosphine ligand in the presence of a solvent.

20. The catalyst of claim 19 wherein the solvent comprises an ether.

21. The catalyst of claim 20 wherein the solvent is methyl tertiary butyl ether.

22. The catalyst of claim 19 wherein the ruthenium 0) compound is reacted with the ditertiary phosphine ligand at a temperature within the range of 90 to 130° C.

23. The catalyst of claim 19 wherein complex (A) is caused to undergo a redox reaction with a cobalt(0) carbonyl compound at a temperature of within the range of 9 to 130° C.

* * * * *